United States Patent [19]
Kischka et al.

[11] Patent Number: 5,609,168
[45] Date of Patent: Mar. 11, 1997

[54] HAIR TREATMENT COMPOSITION AND METHOD OF USING SAME

[75] Inventors: Karl-Heinz Kischka, Darmstadt; Ernst Flemming, Heusenstamm, both of Germany

[73] Assignee: Wella Aktiengesellschaft, Darmstadt, Germany

[21] Appl. No.: 439,262

[22] Filed: May 11, 1995

[30] Foreign Application Priority Data

Jun. 3, 1994 [DE] Germany .................. 44 19 457.9

[51] Int. Cl.$^6$ ............................................. A45D 7/04
[52] U.S. Cl. ................. 132/204; 132/202; 132/203; 132/205; 132/208; 132/209
[58] Field of Search ................... 132/202, 203, 132/204, 205, 209, 208; 424/63, 70.13, 70.15, 70.16, 47; 8/405, 406

[56] References Cited

U.S. PATENT DOCUMENTS

| | | | |
|---|---|---|---|
| 4,134,412 | 1/1979 | Gross et al. | 132/203 |
| 4,592,908 | 6/1986 | Wajaroff et al. | 132/202 |
| 4,772,690 | 9/1988 | Lang et al. | 424/47 |
| 4,780,310 | 10/1988 | Lang et al. | 424/47 |
| 4,900,545 | 2/1990 | Wisotzki et al. | 424/70.13 |

FOREIGN PATENT DOCUMENTS 0460154  12/1990  European Pat. Off. .

*Primary Examiner*—Gene Mancene
*Assistant Examiner*—Philogene Pedro
*Attorney, Agent, or Firm*—Michael J. Striker

[57] ABSTRACT

The aqueous-alcoholic hair treatment composition contains 0.1 to 10 percent by weight of one or more film-forming ionic, anionic and/or amphoteric polymer; 0.1 to 9 percent by weight of one or more amphoteric surfactant; 0.1 to 40 percent by weight of one or more alcohol having 2 to 4 carbon atoms and 0.01 to 2.0 percent by weight of one or more organic acid. The aqueous-alcoholic hair treatment composition is also free of cationic surfactants. The aqueous-alcoholic hair treatment composition can be used as a permanent wave pre-treatment agent for treating hair prior to winding the hair on permanent wave curlers.

14 Claims, No Drawings

HAIR TREATMENT COMPOSITION AND METHOD OF USING SAME

BACKGROUND OF THE INVENTION

The present invention relates to an aqueous-alcoholic composition for treating hair, which is free of cationic surfactants and contains a combination of at least one film-forming cationic, anionic and/or amphoteric polymer with an amphoteric surfactant, a $C_2$- to $C_4$-alcohol and an organic acid. It also relates to methods of using that composition.

The physical, chemical and morphological properties of hair are influenced negatively by many different kinds of actions. Thus the hair is severely stressed and damaged, by cosmetic treatments, such as repeated bleaching, permanent wave treatments and hair dyeing, and also frequent washing with de-oiling surfactants, by climatic influences such as moisture and temperature differences or the intensive action of sunlight and by mechanical treatment, such as brushing, combing and rubbing, especially in the vicinity of the hair tips, while the hair in the vicinity of the roots has a healthy undamaged structure. The greatly differing hair structure of the hair roots and the hair tips is a significant problem during the permanent wave treatment of hair. When the waving effectiveness of the permanent shaping composition for the hair is adapted to compensate for the worn and damaged hair tips, one generally obtains only an unsatisfactory permanent shaping of the hair at the hair roots. When one, in contrast, adjusts the effectiveness of the permanent shaping composition, for the undamaged hair at the hair roots, the hair at the worn hair tips can be damaged so very badly that curliness is significantly reduced or the individual hairs can even be broken.

During the permanent shaping of the hair performed with keratin-reducing shaping agents generally one first washes and then moistens the hair rubbed with a hand towel with a portion of a permanent shaping composition, then divides it into strands, winds these strands individually on permanent wave curlers and subsequently moistens the hair with the remaining portion of the permanent shaping composition. After finishing the permanent shaping process the hair is rinsed with water, then fixed oxidatively, subsequently removed from the curlers, rinsed with fresh water and, if necessary, after-treated with a treatment preparation.

This process has however several disadvantages. This sort of permanent shaping method can cause injury to the hands of the beauty shop personnel performing the treatment (e.g. allergies or other skin conditions), since the hands can come into contact with the permanent shaping composition for a total time amounting to about 20 minutes required for the curling or waving process. Moreover the above-described method is not very safe for the hair, since hair softening due to moistening of the hair with the hair shaping composition can very easily lead to an overstretching of the hair during the curling process on the curlers and, as a result of that, to hair breaking and hair falling out.

Moreover the hair is very strongly stressed after a hair shaping treatment so that an after-treatment with a hair care composition is necessary to again impart to the hair a natural touch and look.

SUMMARY OF THE INVENTION

It is an object of the present invention to provide a composition for treatment of hair, which protects the hair, especially the hair tips, during the permanent shaping process and thus permits a uniform shaping of hair.

It is also an object of the present invention to provide a composition for treatment of hair, which protects the hair, especially the hair tips, and which has satisfactory luster giving properties without stressing the hair.

According to the invention, the hair treatment composition is an aqueous-alcoholic composition containing:

A) 0.1 to 10 percent by weight of at least one film-forming cationic, anionic and/or amphoteric polymer, B) 0.1 to 9 percent by weight of at least one amphoteric surfactant, C) 0.1 to 40 percent by weight of at least one $C_2$- to $C_4$-alcohol, and D) 0.01 to 2.0 percent by weight of at least one organic acid; and not containing a cationic surfactant.

This hair treatment composition achieves the objects of the invention in an outstanding manner.

In a preferred embodiment of the invention component (A) is advantageously contained in an amount of from 0.1 to 4 percent by weight.

Suitable film-forming cationic polymers which can be used as component (A) include quaternarized vinylpyrrolidone/dimethylaminoethylmethacrylate copolymers, dimethyl-diallylammonium chloride polymers, quaternary acrylamide/dimethyldiallylammonium chloride copolymers, quaternarized methylvinylimidazolinium/vinylpyrrolidone copolymers and cationic chitosan derivatives.

Suitable quaternary vinylpyrrolidone/dimethylaminoethylmethacrylate copolymers are for example sold by GAF Co., New York, USA in the form of a 20 percent aqueous solution under the tradename Gafquat$^R$ 755N and in the form of a 50 percent aqueous solution in ethanol under the tradename Gafquat$^R$ 734. Suitable dimethyldiallylammonium chloride polymers which can be used as component (A) according to the invention are sold, for example, by Merck & Co. Inc., New Jersey, USA, in the form of a 40 percent aqueous solution under the tradename Merquat$^R$ 100 and suitable quaternary acrylamide/dimethyldiallylammonium chloride copolymers are sold by the same company in the form of an 8 percent aqueous solution under the tradename Merquat$^R$ 550.

Quaternary methylvinylimidazolinium/vinylpyrrolidone copolymers suitable for use as component (A) are marketed under the tradename Luviquat$^R$ FC 905 in the form of a 40 percent aqueous solution by BASF AG, Ludwigshafen, Germany.

Film-forming anionic polymers which are suitable for use as component (A) according to the invention are, for example, marketed as Shellac or vinylacetate/crotonic acid copolymers, which are marketed, e.g., by Hoechst AG, Frankfurt, Germany, in the form of a 60 percent aqueous-alcoholic solution of water and isopropanol under the tradename Aristoflex$^R$ A and Delft-National GmbH, Frankfurt, Germany under the tradename Resyn$^R$ 28-1310.

A film-forming amphoteric polymer which is suitable as component (A) in the composition according to the invention is octylacrylamide/acrylate/butylaminoethyl/methacrylate copolymer, which is marketed by National Starch and Chem. Co., New Jersey, USA under the trade name Amphomer$^R$.

Of the film-forming cationic, anionic and amphoteric polymers the film-forming cationic polymers are particularly preferred in the hair treatment composition according to the invention.

The hair treatment composition according to the invention advantageously contains 0.1 to 4 percent by weight of at least one amphoteric surfactant as component (B).

Alkylbetaine, alkylaminobetaine, fatty acid amidoalkylbetaine and fatty acid amidoalkylsulfobetaine are all suitable for the amphoteric surfactant used as component (B).

The amphoteric surfactant, component B, is advantageously either fatty acid amidoalkylbetaines, fatty acid amidoalkylsulfobetaines or mixtures thereof.

Coconut oil fatty acid amidopropyl betaine is advantageously contained as component (B), which for example is marketed by Goldschmidt, Essen, Germany, in the form of a 30 percent aqueous solution under the Trademark Tego Betain$^R$ L7, and/or 3-(3-coconut oil fatty acid amidopropyl) dimethylammonium-2-hydroxypropane sulfonate, which, e.g., is marketed in the form of a 50 percent aqueous solution under the Trademark Rewoteric$^R$ AM-CAS of Rewo Chemische Werke GmbH, Steinau, Germany, under the tradename Mirataine$^R$ CBS by Miranol Chem. Co. Inc., New Jersey, USA and under the tradename Schercotaine$^R$ SCAB-A by Scher Chem Inc., New Jersey, USA.

Component (C) is present in the hair treatment composition of the invention in an amount of 5 to 25 percent by weight in a preferred embodiment of the invention. The alcohols which are suitable for use as component (C) include straight chain or branched $C_2$- to $C_4$-alkyl chains. Ethanol, isopropanol or mixtures thereof are particularly preferred as component (C).

The component (D) is present in an amount of from 0.01 to 1 percent by weight in a preferred embodiment of the invention.

The at least one organic acid used as component (D) in the hair treatment composition according to the invention, advantageously can be selected from the group consisting of citric acid, tartaric acid, glyoxalic acid, lactic acid and formic acid.

A preferred embodiment of the hair treatment composition according to the invention can also contain, in addition to components (A) to (D), 0.1 to 10 percent by weight, especially 0.1 to 4 percent by weight, of polyvinylpyrrolidone and/or chitosan. Polyvinylpyrrolidone is particularly preferred as an additive.

Suitable polyvinylpyrrolines are marketed under the tradename of Luviskol$^R$ K 90 by BASF, Ludwigshafen, Germany, and under the tradename PVP/K$^R$ by ISP, Surrey, Great Britain.

The hair treatment composition according to the invention can contain, in addition to the components (A) to (D), 0.1 to 5 percent by weight of at least one nonionic surfactant.

Nonionic surfactants according to the invention which can be used as nonionic surfactants include alkylpolyglucosides, e.g. laurylpolyglucose, which is marketed in the form of a 50 percent aqueous solution under the tradename Plantaren$^R$ 1200 CS/UP by Henkel KGaA, Düsseldorf, Germany.

The hair treatment composition according to the invention advantageously has a pH of 2.5 to 6.9, especially from 2.5 to 4.5.

The hair treatment composition according to the invention can advantageously also contain all those ingredients, which are commonly used in hair treatment compositions, for example, especially, foam synergistic agents, foam stabilizers, sequestering agents; natural products; pigments; perfume oils in an amount of from 0.05 to 3.0 percent by weight; turbidity inducing agents, for example ethylene glycol distearate, in an amount of from about 0.05 to 5.0 percent by weight; pearlescence imparting agents, such as a mixture of fatty acid monoalkylolamide and ethyleneglycol distearate, in an amount of about 1.0 to 10.0 percent by weight; thickening agents, such as coconut oil fatty acid diethanol amide or hydroxyalkyl cellulose, in an amount of 0.5 to 10.0 percent by weight; buffer substances, such as sodium citrate or sodium phosphate, in an amount of 0.1 to 1.0 percent by weight; dyes, such as fluorescein-sodium salt, Gelb ZN3 (C.I. 47 055), in an amount of 0.1 to 1.0 percent by weight; additional hair care substances, such as lanolin derivates, keratin hydrolyzates, cholesterin and pantothenic acid, in an amount of 0.1 to 10 percent by weight; moreover physiologically compatible inorganic salts, such as, e.g., sodium chloride and sodium sulfate; as well as additional moisturizing agents; light protective substances; antioxidants, complex formers, anti-scaling agents, cosmetic oils, waxes and preservative materials. The composition of the invention can contain the above ingredients in so far as those ingredients appear useful and appropriate and are compatible with the components of the invention.

The composition according to the invention advantageously has a water content of 70 to 90 percent by weight.

The hair treatment composition according to the invention is in the form of a preparation which is not rinsed from the hair after it is applied and can be used as a hair structure regenerator prior to setting the hair in a hair-do, a hair drying wave or hot-wave the hair or prior to a permanent wave treatment and as a curl restoring agent for permanent or natural wave treatments of the hair.

The hair treatment composition according to the invention has outstanding conditioning properties. This hair treatment composition imparts to the hair a beautiful luster without impairing the retention of the permanent wave by the hair. The combability and the feel of the hair are clearly improved by use of the hair treatment composition according to the invention.

The hair treatment composition according to the invention is advantageously used as a permanent wave pre-treatment agent, which means that it is applied to the hair prior to winding the hair on curlers.

The hair treatment composition according to the invention used as a permanent wave pre-treatment agent during permanent wave process causes a uniform shaping of hair during the permanent wave process. The sensitive hair tips and structurally damaged hair are protected by use of the hair treatment composition according to the invention as the permanent wave pre-treatment agent during permanent shaping of hair so that a careful and safe permanent shaping of hair is possible.

Particularly structurally damaged hair has porous regions preponderantly in the scale layer, but also in the fiber stem. These porous regions are neutralized by the hair treatment composition according to the invention, which advantageously demonstrably surrounds the damaged regions of the hair, so that the hair damaging action of the permanent wave solution can be avoided.

Also the closing of the scale layer (Cuticle) of the hair, particularly by component (D) of the composition according to the invention, is promoted so that the diffusion of the waving ingredients of the permanent wave solution in the hair is delayed.

The curling of the hair on the permanent wave curlers is considerably simplified by use of the aqueous-alcoholic hair treatment composition according to the invention as the permanent wave pre-treatment means. Furthermore the hair treatment composition according to the invention, causes, when it is applied prior to a permanent shaping of the hair, a clear improvement in the springiness and elasticity of the permanently shaped hair.

The hair shaping composition according to the invention is advantageously in the form of an aqueous-alcoholic solution and can be sprayed using a propellant or with the help of mechanically-operated spraying or foam-making device or delivered as a foam.

If the hair treatment composition is sprayed with the help of a propellant, it is advantageously prepared with from 3 to 20 percent by weight of propellant means and is filled in a pressurized container.

For example lower alkanes, such as n-butane, i-butane and propane or also their mixtures with dimethylether, and also with propellant gases under pressure, such as $N_2$, $N_2O$, and $CO_2$ and mixtures thereof, can be used as the propellant.

"Mechanical spraying or foam producing devices" means devices which permit the spraying or application of foam without use of a propellant. Suitable mechanical spraying devices can include spray pumps or an elastic container provided with a spray valve, in which the cosmetic composition according to the invention is filled under pressure so that the container material is stretched. The hair treatment composition of the invention is then delivered from the elastic container continuously when the spray valve is opened as a result of the container contraction.

For example a headpiece on an elastic container described in German Patent Application EP-B 0 460 154 having a foam making device can be used as a suitable mechanical foam producing apparatus.

The present invention further relates to a method for permanent shaping of hair in which one pre-treats the hair with the pre-treatment composition according to the invention prior to curling the hair or winding the hair on permanent wave curlers. Then the hair is dried, moistened with fresh water, wound on the curlers, then treated with a hair shaping composition which is allowed to act on the hair for a predetermined acting time and then rinsed from the hair, then oxidatively after-treated and rinsed with water, subsequently set in a hair-do and then dried. This method of permanent shaping of hair is of course characterized by use of the pre-treatment composition according to the invention.

The hair is washed first with a shampoo in the method according to the invention and, after that, rinsed with water. Subsequently an amount of the hair treatment composition according to the invention sufficient for the permanent shaping pre-treatment, advantageously about 10 to 20 g, of the hair treatment agent according to the invention is applied to the hand-towel-dried hair, advantageously to the hair tips. After a sufficient acting time, which depends on the hair properties amounts to about 5 to 15 minutes, the hair is dried. Then the hair is moistened with water, without however rinsing the permanent wave pre-treatment composition from the hair. The hair is divided in strands and wound on the permanent wave curlers. The diameter of the curlers amounts to about 5 to 35 millimeters. Subsequently the hair is treated with a quantity of the hair shaping composition sufficient for the permanent shaping of hair, advantageously about 60 to 90 g.

A preferred permanent shaping composition for use in the method according to the invention is an aqueous alkaline preparation with a pH of from 7 to 10 which contains a keratin-reducing mercapto compound, such as Cysteine, Cysteamine, N-acetyl-L-cysteine, mercaptocarboxylic acids, for example thioglycolic acid or thiolactic acid, or salts of mercaptocarboxylic acids, such as ammonium and guanidine salts of thioglycolic acid or thiolactic acid, in a concentration of from about 2 to 12 percent by weight.

The required alkalinity is adjusted by addition of ammonia, organic amines, ammonium carbonates, alkali metal carbonates or alkali metal hydrogen carbonates.

The permanent shaping composition for use in the method according to the invention can also be an aqueous acidic or neutral preparation with a pH of from 4.5 to 7 which contains an effective sulfite or mercaptocarboxylic acid ester content.

In the former or first case sodium or ammonium sulfites or the salt of the sulfurous acid with an organic amine, such as monoethanolamines and guanidine, are used in concentrations of about 2 to 12 percent by weight(calculated as $SO_2$). In the latter or last case thioglycolic acid monoglycol ester or thioglycolic acid monoglycerine ester is used in concentrations of 5 to 50 percent by weight (corresponding to a concentration of 2 to 16 percent by weight of free thioglycolic acid). The hair The shaping composition for the permanent shaping of hair can also contain a mixture of the previously-mentioned keratin-reducing compounds.

After an acting time sufficient for the permanent shaping of hair, which, according to hair properties, pH values, shaping effectiveness of the shaping agent and application temperatures, amounts to about 10 to 30 minutes, the hair is rinsed with water and subsequently oxidatively after-treated ("fixed"). The after-treatment composition is, according to the hair feel, applied in an amount of from about 50 to 100 g.

Any conventional after-treatment composition used previously for an oxidative after-treatment can be used for the oxidative after-treatment in the method according to the invention. For example, sodium bromate, potassium bromate, sodium perborate, urea peroxide and hydrogen peroxide can all be used as the effective ingredient in the oxidative after-treatment composition.

The concentration of the oxidizing agent in the oxidative after-treatment composition depends on the differing application times (usually about 5 to 15 minutes) and the application temperatures. The concentration of the oxidizing agent in the aqueous oxidative after-treatment composition is from about 0.5 to 10 percent by weight.

Both the permanent shaping composition and the oxidative after-treatment composition can be in the form of an aqueous solution or emulsion and also in thickened form on an aqueous basis, particularly in the form of a cream, gel or paste. It is possible to fill this composition under pressure in an aerosol can and to dispense the composition from the aerosol can.

Subsequently the curlers are removed. As the case requires, the curled hair can be subjected to an additional oxidative after-treatment. Then the hair is rinsed with water, is set in a hair-do and subsequently dried.

The above-described process according to the invention for the permanent shaping of hair allows a careful and uniform shaping from the hair roots to the hair tips. The hair so treated has an outstanding wet and dry comability, a pleasant feel and a pronounced luster in the dry state as well as a loose, springy and simultaneously permanent wave, particularly in the vicinity of the hair tips.

An additional feature of the present invention resides in a method for treatment of hair which does not involve the subsequent permanent shaping of hair comprising distributing from 10 to 20 g of the hair treatment composition according to the invention on hand-towel dried hair. After a sufficient acting time, which amounts to from 5 to 15 minutes depending on the hair properties, the hair is dried. Subsequently the hair is moistened with water, if necessary put in a hair-do and then dried again.

The invention also comprises a method of treating natural or permanently waved hair, which is a curl restoration method, in which 10 to 20 g of the hair treatment composition according to the invention are distributed on dry or moistened natural or permanently waved hair by spraying and subsequently manually spread over the hair, advantageously with a hand, then the hair is set in a hair-do and subsequently dried.

The hair treated with the hair treatment composition according to the invention in the above-described manner has an outstanding wet and dry combability, a pleasant feel and a pronounced luster in the dried state.

EXAMPLES

| Example 1: | Hair Treatment Composition |
|---|---|
| 0.600 g | Polyvinylpyrrolidone |
| 0.200 g | Vinylpyrrolidone/dimethylaminoethyl-methacrylate copolymer (Gafquat® 755N of GAF Co./USA) |
| 0.400 g | 3-(3-coconut oil fatty acid amidopropyl)-dimethylammonium-2-hydroxypropane sulfonate |
| 0.010 g | Keratin hydrolyzate |
| 0.100 g | Glyoxalic acid |
| 12.000 g | Ethanol |
| 86.690 g | Water |
| 100.00 g | |

| Example 2: | Hair Treatment Composition |
|---|---|
| 0.600 g | Polyvinylpyrrolidone |
| 0.200 g | Methylvinylimidazolinium/vinyl-pyrrolidone copolymer (Luviquat® FC 905 of BASF AG, Germany) |
| 0.450 g | Coconut oil fatty acid amidopropylbetaine |
| 0.020 g | Keratin hydrolyzate |
| 0.200 g | Citric acid |
| 10.000 g | Isopropanol |
| 88.530 g | Water |
| 100.00 g | |

| Example 3: | Hair Treatment Composition |
|---|---|
| 1.280 g | Methylvinylimidazolinium/vinyl-pyrrolidone copolymer (Luviquat® FC 905 of BASF AG, Germany) |
| 0.300 g | Coconut oil fatty acid amidopropylbetaine |
| 0.500 g | Chamomile blood extract (Extrapon® Chamonile Special 2/033021 of Dragoco, Hozminden, Germany) |
| 0.160 g | Keratin hydrolyzate |
| 0.250 g | Citric acid |
| 15.000 g | Ethanol |
| 82.510 g | Water |
| 100.00 g | |

| Example 4: | Hair Treatment Composition |
|---|---|
| 0.640 g | Dimethyldiallylammonium chloride-polymer (Merquat® 100 of GAF Co, USA) |
| 0.300 g | Coconut oil fatty acid amidopropylbetaine |
| 0.500 g | Chamomile blood extract (Extrapon® Chamomile Special 2/033021 of Dragoco, Hozminden, Germany) |
| 0.250 g | Citric acid |
| 15.000 g | Ethanol |

-continued

| Example 4: | Hair Treatment Composition |
|---|---|
| 83.310 g | Water |
| 100.00 g | |

| Example 5: | Hair Treatment Composition |
|---|---|
| 0.144 g | Acrylamide/dimethyldiallylammonium chloride copolymer (Merquat® 550 of GAF Co, USA) |
| 0.300 g | Coconut oil fatty acid amidopropylbetaine |
| 0.160 g | Keratin hydrolyzate |
| 0.500 g | Chamomile blood extract (Extrapon® Chamomile Special 2/033021 of Dragoco, Hozminden, Germany) |
| 0.250 g | Citric acid |
| 15.000 g | Ethanol |
| 83.646 g | Water |
| 100.00 g | |

| Example 6: | Hair Treatment Composition |
|---|---|
| 0.450 g | Vinylpyrrolidone/dimethylaminoethyl methacrylate copolymer (Gafquat® 734 of GAF Co, USA) |
| 0.300 g | Coconut oil fatty acid amidopropylbetaine |
| 0.160 g | Keratin hydrolyzate |
| 0.500 g | Chamomile blood extract (Extrapon® Chamomile Special 2/033021 of Dragoco, Hozminden, Germany) |
| 0.250 g | Citric acid |
| 15.450 g | Ethanol |
| 82.890 g | Water |
| 100.00 g | |

| Example 7: | Hair Treatment Composition |
|---|---|
| 0.280 g | Vinylpyrrolidone/dimethylaminoethyl-methacrylate copolymer (Gafquat® 755N of GAF Co./USA) |
| 0.300 g | Coconut oil fatty acid amidopropylbetaine |
| 0.500 g | Chamomile blood extract (Extrapon® Chamomile Special 2/033021 of Dragoco, Hozminden, Germany) |
| 0.250 g | Citric acid |
| 15.000 g | Ethanol |
| 83.670 g | Water |
| 100.00 g | |

| Example 8: | Hair Treatment Composition |
|---|---|
| 0.600 g | Vinylacetate/crotonic acid copolymer (Aristoflex® A of Hoechst AG, Germany) |
| 0.800 g | laurylpolyglucose |
| 0.150 g | Coconut oil fatty acid amidopropylbetaine |
| 0.120 g | Keratin hydrolyzate |
| 0.100 g | Lactic acid |
| 25.000 g | Ethanol |

| Example 8: | Hair Treatment Composition |
|---|---|
| 73.230 g | Water |
| 100.00 g | |

All percentages are percents by weight unless otherwise indicated.

While the invention has been illustrated and described as embodied in a hair treatment composition and method of using it, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. An aqueous-alcoholic hair treatment composition comprising:
   A) from 0.1 to 10 percent by weight of at least one film-forming compound selected from the group consisting of cationic, anionic and amphoteric film-forming polymers;
   B) from 0.1 to 9 percent by weight of at least one amphoteric surfactant;
   C) from 0.1 to 40 percent by weight of at least one $C_2$- to $C_4$-alcohol; and
   D) from 0.01 to 2.0 percent by weight of at least one organic acid; and not containing a cationic surfactant.

2. The composition as defined in claim 1, containing from 0.1 to 4 percent by weight of said at least one film-forming compound.

3. The composition as defined in claim 1, wherein said at least one amphoteric surfactant is selected from the group consisting of fatty acid amidoalkylbetaines, fatty acid amidoalkylsulfobetaines and mixtures thereof.

4. The composition as defined in claim 1, containing from 0.1 to 4 percent by weight of said at least one amphoteric surfactant.

5. The composition as defined in claim 1, containing from 5 to 25 percent by weight of said at least one $C_2$- to $C_4$-alcohol.

6. The composition as defined in claim 1, wherein said at least one $C_2$- to $C_4$-alcohol is selected from the group consisting of ethanol, isopropanol and mixtures thereof.

7. The composition as defined in claim 1, containing from 0.01 to 1 percent by weight of said at least one organic acid.

8. The composition as defined in claim 1, wherein said at least one organic acid is selected from the group consisting of citric acid, tartaric acid, glyoxalic acid, lactic acid and formic acid.

9. The composition as defined in claim 1, further comprising 0.1 to 10 percent by weight of an additional substance selected from the group consisting of polyvinylpyrrolidone, chitosan and mixtures thereof.

10. The composition as defined in claim 1, further comprising from 0.1 to 5 percent by weight of at least one nonionic surfactant.

11. A process of permanent shaping of hair, said process comprising the steps of:
   a) applying a permanent wave pre-treatment composition to hair;
   b) drying the hair;
   c) moistening the hair with water;
   d) winding the hair on curlers;
   e) after the applying of the permanent wave pre-treatment composition in step a) and the winding of the hair on curlers in step d), applying a hair shaping composition to the hair;
   f) after the applying of the hair shaping composition of step e), allowing the hair shaping composition to act on the hair for a predetermined time interval sufficient for a permanent shaping of the hair and then rinsing the hair with water;
   g) after the applying of the hair shaping composition and the rinsing of steps e) and f), treating the hair with an oxidative after-treatment composition and then, after the treating of the hair with the oxidative after-treatment composition, again rinsing with water; and
   h) after the treating with the oxidative after-treatment composition of step g), setting the hair in a hair-do and again drying the hair;
   wherein said permanent wave pre-treatment composition comprises:
   A) from 0.1 to 10 percent by weight of at least one film-forming compound selected from the group consisting of cationic, anionic and amphoteric film-forming polymers;
   B) from 0.1 to 9 percent by weight of at least one amphoteric surfactant;
   C) from 0.1 to 40 percent by weight of at least one $C_2$- to $C_4$-alcohol; and
   D) from 0.01 to 2.0 percent by weight of at least one organic acid; and not containing a cationic surfactant.

12. The process as defined in claim 11, wherein 10 to 20 g of said permanent wave pre-treatment composition is applied during said applying of the permanent wave pre-treatment composition.

13. A method of treating hair, said method comprising the steps of:
   a) washing the hair and drying the hair with a hand-towel;
   b) after the washing and drying of step a), distributing on the hair from 10 to 20 g of an aqueous-alcoholic hair treatment composition including from 0.1 to 10 percent by weight of at least one film-forming compound selected from the group consisting of cationic, anionic and amphoteric film-forming polymers; from 0.1 to 9 percent by weight of at least one amphoteric surfactant; from 0.1 to 40 percent by weight of at least one $C_2$- to $C_4$-alcohol and from 0.01 to 2.0 percent by weight of at least one organic acid; and not containing a cationic surfactant;
   c) after the distributing of step b), drying the hair; and
   d) moistening the hair again with water and then again drying the hair.

14. A method of treating natural and permanent waved hair, said method comprising the steps of:
   a) distributing on natural or permanently waved hair dry or moistened with water from 10 to 20 g of an aqueous-alcoholic hair treatment composition including from 0.1 to 10 percent by weight of at least one film-forming compound selected from the group consisting of cationic, anionic and amphoteric film-forming polymers; from 0.1 to 9 percent by weight of at least one amphoteric surfactant; from 0.1 to 40 percent by weight of at least one $C_2$- to $C_4$-alcohol and from 0.01 to 2.0 percent by weight of at least one organic acid; and not containing a cationic surfactant;

b) after the distributing in step a), setting the hair in a hair-do; and c) after the setting of the hair in step b), drying the hair.

* * * * *